US009884883B2

(12) United States Patent
Lohitharn et al.

(10) Patent No.: US 9,884,883 B2
(45) Date of Patent: Feb. 6, 2018

(54) PRODUCTION OF RHAMNOLIPID COMPOSITIONS

(71) Applicant: Logos Technologies, LLC, Fairfax, VA (US)

(72) Inventors: Nattaporn Lohitharn, Chantilly, VA (US); Daniel Derr, San Diego, CA (US)

(73) Assignee: Logos Technologies, LLC, Fairfax, VA (US)

( * ) Notice: Subject to any disclaimer, the term of this patent is extended or adjusted under 35 U.S.C. 154(b) by 0 days.

(21) Appl. No.: 14/992,995

(22) Filed: Jan. 11, 2016

(65) Prior Publication Data

US 2016/0272667 A1    Sep. 22, 2016

Related U.S. Application Data

(60) Provisional application No. 62/102,310, filed on Jan. 12, 2015, provisional application No. 62/141,679, filed on Apr. 1, 2015, provisional application No. 62/157,019, filed on May 5, 2015.

(51) Int. Cl.
*C07H 15/04* (2006.01)
*A61L 2/18* (2006.01)
*C07H 1/06* (2006.01)

(52) U.S. Cl.
CPC .............. *C07H 15/04* (2013.01); *A61L 2/18* (2013.01); *A61L 2/186* (2013.01); *C07H 1/06* (2013.01)

(58) Field of Classification Search
CPC A61L 2/18; A61L 2/186; C07H 15/04; C07H 1/06
See application file for complete search history.

(56) References Cited

U.S. PATENT DOCUMENTS

| | | | |
|---|---|---|---|
| 4,628,030 A | 12/1986 | Kaeppeli | |
| 4,814,272 A | 3/1989 | Wagner | |
| 4,902,512 A | 2/1990 | Ishigami | |
| 5,013,654 A | 5/1991 | Banerjee | |
| 5,656,747 A | 8/1997 | Mixich | |
| 6,060,287 A * | 5/2000 | Rocha | C07H 15/04 435/134 |
| 6,953,849 B2 | 10/2005 | Vali | |
| 7,202,063 B1 | 4/2007 | Gunther | |
| 9,005,928 B2 * | 4/2015 | Schaffer | A01N 43/16 435/252.34 |
| 2011/0306569 A1 | 12/2011 | Yin | |
| 2014/0296125 A1 | 2/2014 | Kuppert | |
| 2014/0148588 A1 | 5/2014 | Schilling | |
| 2014/0235561 A1 | 8/2014 | Blank | |
| 2014/0296168 A1 | 10/2014 | Schilling | |
| 2015/0011741 A1 | 1/2015 | Blank | |
| 2015/0247151 A1 | 9/2015 | Schaffer | |

FOREIGN PATENT DOCUMENTS

| | | |
|---|---|---|
| CN | 1891831 A | 1/2007 |
| CN | 1907916 A | 2/2007 |
| CN | 1908180 A | 2/2007 |
| CN | 1974589 A | 6/2007 |
| CN | 101173210 A | 5/2008 |
| CN | 101173238 A | 5/2008 |
| CN | 101182560 A | 5/2008 |
| CN | 101265488 A | 9/2008 |
| CN | 101407831 A | 4/2009 |
| CN | 101538604 A | 9/2009 |
| CN | 101613725 A | 12/2009 |
| CN | 101705200 A | 5/2010 |
| CN | 101787057 A | 7/2010 |
| CN | 101845468 A | 9/2010 |
| CN | 101948786 A | 1/2011 |
| CN | 101948787 A | 1/2011 |
| CN | 102250790 A | 11/2011 |
| CN | 102432643 A | 5/2012 |
| CN | 102766172 A | 11/2012 |
| CN | 102796781 A | 11/2012 |
| CN | 102851059 A | 1/2013 |
| CN | 103146742 A | 6/2013 |
| CN | 103589765 A | 2/2014 |
| CN | 103966282 A | 8/2014 |
| CN | 104099388 A | 10/2014 |
| CN | 104450825 A | 3/2015 |
| CN | 104498566 A | 4/2015 |
| EP | 2410039 A1 | 1/2012 |
| JP | 1075796 A | 3/1998 |
| JP | 2003052368 A | 2/2003 |
| KR | 20060018783 A | 3/2006 |
| KR | 20070027151 A | 3/2007 |
| KR | 100940231 B1 | 2/2010 |
| KR | 1020130084760 A | 7/2013 |
| WO | 2012010406 A1 | 1/2012 |

(Continued)

OTHER PUBLICATIONS

Banat et al. (2010) "Microbial biosurfactants production, applications and future potential", Appl. Microbiol. Biotechnol. 87:427-444.
Desai et al. (1997) "Microbial Production of Surfactants and Their Commercial Potential", Microbiol. Mol. Biol. Rev. 61: 47-64.
Heyd et al. (2008) "Development and trends of biosurfactant analysis and purification using rhamnolipids as an example", Anal. Bioanal. Chem. 391:1579-1590.
Jarvis et al. (1949) "A Glyco-lipide Produced by Pseudomonas Aeruginosa", J. Am. Chem. Soc. 71: 4124.
Lebrón-Paler (2008) "Solution and interfacial characterization of rhamnolipid biosurfactant from P. aeruginosa ATCC 9027", PhD Dissertation University of Arizona.
Long et al. (2012) "Two-step ultrafiltration of rhamnolipids using PSU-g-PEG membrane", J. Membrane Sci. 409-410: 105-112.
Marchant et al. (2012) "Microbial biosurfactants: challenges and opportunities for future exploitation", Trends in Biotechnology 30: 558-565.
Muller et al. (2012) "Rhamnolipids—Next generation surfactants?", J. Biotechnol. 162(4):366-80.

(Continued)

*Primary Examiner* — Snigdha Maewall (74) *Attorney, Agent, or Firm* — Cheryl H. Agris; Agris & von Natzmer LLP (57) ABSTRACT

Provided are organic solvent free methods for obtaining compositions comprising one or more rhamnolipids as well as compositions obtainable from said methods.

10 Claims, 2 Drawing Sheets

(56) References Cited

FOREIGN PATENT DOCUMENTS

| WO | 2014039940 A1 | 3/2014 |
|---|---|---|
| WO | 2015030702 A2 | 3/2015 |
| WO | 2015085411 A1 | 6/2015 |
| WO | 2015091294 A1 | 6/2015 |

OTHER PUBLICATIONS

Mulligan et al. (1990) "Recovery of Biosurfactants by Ultrafiltration", J. Chem. Tech. Biotechnol. 47: 23-29.

Padilha et al. (2015) "Prediction of rhamnolipid breakthrough curves on activated carbon and Amberlite XAD-2 using Artificial Neural Network and Group Method Data Handling models", J. Mol. Liquids 206: 293-299.

Randhawa et al. (2014) "Rhamnolipid biosurfactants—past, present, and future scenario of global market", Frontiers in Microbiology 5:1-7.

Rikalovic et al. (2013) "Comparative Analysis of Rhamnolipids from Novel Environmental Isolates of Pseudomonas aeroginosa", J. Surfact. Deterg. 16:673-682.

Rikalovic et al. (2012) "Production and characterization of rhamnolipids from Pseudomonas aeruginosa san-ai", Journal of the Serbian Chemical Society 77: 27-42.

Sarachat et al., (2010) "Purification and concentration of a rhamnolipid biosurfactant produced by Pseudomonas aeruginosa SP4 using foam fractionation", Bioresource Technology 101: 324-330.

Smyth et al. (2010) "Isolation and Analysis of Low Molecular Weight Microbial Glycolipids", in Handbook of Hydrocarbon and Lipid Microbiology, K. N. Timmis (ed.), Springer-Verlag, Berlin, pp. 3705-3723.

Witek-Krowiak et al. (2011) "Ultrafiltrative separation of rhamnolipid from culture medium", World Journal of Microbiology and Biotechnology 27: 1961-1964.

Zhang et al. "Separation and purification of six biosurfactant rhamnolipids by high-speed countercurrent chromatography utilizing novel solvent selection method", Separation Science and Technology, , 51:673-680 (posted Nov. 24, 2015).

PCT/US2016/30271, International Search Report and Written Opinion, dated May 26, 2016.

* cited by examiner

PRODUCTION OF RHAMNOLIPID COMPOSITIONS

TECHNICAL FIELD

Provided are organic solvent-free processes for obtaining composition comprising rhamnolipids as well as said compositions.

BACKGROUND

Rhamnolipids (RLs) are interface-active glycolipids produced by various bacterial species. RLs consist of one (monorhamnosylipids or mono-rhamnolipids) or two rhamnose units (dirhamnosylipids or di-rhamnolipids) and one or two (predominantly two) 3-hydroxy fatty acid residues. Rhamnolipids have particular surface-active properties such as, for example, a strong foaming ability, and are of interest for highly diverse technical applications, particularly as surfactants (reviewed in Randhawa et al. (2014) "Rhamnolipid biosurfactants—past, present, and future scenario of global market", Frontiers in Microbiology 5:1-7; Muller et al. (2012) "Rhamnolipids—Next generation surfactants?", J Biotechnol 162(4):366-80; Banat et al. (2010) "Microbial biosurfactants production, applications and future potential" Appl Microbiol Biotechnol 87:427-444). Examples of potential applications include: (1) bioremediation and enhanced oil recovery (EOR) since they efficiently remove crude oil and heavy metals from contaminated soil and facilitate bioremediation of oil spills due to their emulsification properties; (2) cosmetics: including cosmeceuticals for example for wound healing, burns, psoriasis and wrinkles; (3) detergents and cleaners: particularly for laundry products, shampoos and soaps given their surface active and emulsification properties and (4) agriculture. Rhamnolipids are currently available in an agricultural anti-fungal product marketed as ZONIX™ (Proptera LLC).

Interest in RLs has increased since they can be prepared by means of fermentation based on renewable raw materials. However, rhamnolipids have only been available on the market in small amounts and at high prices partially due to cumbersome downstream processing methods. Various methods have been disclosed for producing rhamnolipids (reviewed in, for example, Heyd et al. (2008) "Development and trends of biosurfactant analysis and purification using rhamnolipids as an example", Anal Bioanal Chem 391: 1579-1590 and Smyth et al. (2010) "Isolation and Analysis of Low Molecular Weight Microbial Glycolipids", in Handbook of Hydrocarbon and Lipid Microbiology, K. N. Timmis (ed.), Springer-Verlag, Berlin, pp. 3705-3724; Desai et al. (1997) "Microbial Production of Surfactants and Their Commercial Potential", Microbiol. Mol. Biol. Rev. 61: 47-64 and also disclosed in for example U.S. Pat. No. 5,656,747, U.S. Pat. No. 4,628,030, US20140148588, CN102796781, CN102766172, CN101787057, CN101845468, CN102432643, CN1908180, KR1020060018783).

Currently, the most common isolation procedure for rhamnolipids involves autoclaving fermentation broth right after fermentation is complete, followed by acidifying to precipitate rhamnolipids out. The solid rhamnolipids that result are contaminated with solid cellular material from the organism used in the fermentation. RLs are isolated from these cellular solids by extracting them into an organic solvent such as ethyl acetate. After stripping the ethyl acetate, a concentrated oily form of the product results. However, the solvent extraction process brings along any hydrophobic impurities with it, potentially including unconsumed triacyl glyceride oil and antifoam from the fermentation process. Examples of other methods disclosed include (1) aluminum sulphate precipitation of fermentation broth followed by extraction with organic solvent; (2) continuous ultrafiltration; (3) column chromatography (see, for example, Lebrón-Paler A (2008) "Solution and interfacial characterization of rhamnolipid biosurfactant from $P.$ aeruginosa ATCC 9027" PhD Dissertation University of Arizona, CN101787057, CN101407831, CN1908180) using either adsorption, ion exchange, reversed phase or normal phase columns which may be performed in combination with the precipitation step; (4) countercurrent chromatography (Zhang et al. "Separation and purification of six biosurfactant rhamnolipids by high-speed countercurrent chromatography utilizing novel solvent selection method", Separation Science and Technology, in press (posted Nov. 24, 2015)); (5) selective crystallization followed by extraction or (6) foam fractionation/adsorption (see, for example, US 2015/0011741; Sarachat et al., (2010) "Purification and concentration of a rhamnolipid biosurfactant produced by Pseudomonas aeruginosa SP4 using foam fractionation", Bioresource Technology 101: 324-330). However, all of these methods have various disadvantages as well (e.g., expensive, do not scale well, resource intensive, etc.).

SUMMARY

Provided is an organic solvent-free process for obtaining composition comprising rhamnolipids comprising:
(a) providing an aqueous medium comprising at least one rhamnolipid (RL);
(b) non-filtration based sterilization of said medium provided in (a);
(c) separating a RL containing phase from waste in said sterilized medium in (b) to obtain said composition The final product using the method set forth above comes from a natural process, has not been chemically modified, and has not come in contact with any petroleum based organic solvents. The process or method set forth above eliminates the use of petroleum derived chemical solvents to extract rhamnolipids from aqueous medium (e.g., fermented medium or broth) and thus, it significantly reduces the production cost. Furthermore, the final rhamnolipid solution is naturally derived.

In a particular embodiment, the composition comprising rhamnolipids is a clarified broth comprising at least about 5%, 6%, 7%, 8%, 9%, or 10% rhamnolipids by weight, wherein said method further comprises after step (a) and before step (b), (1) aging said medium provided in step (a) to obtain aged and sterilized medium. Also provided is a composition comprising said aged and sterilized medium obtainable from the process set forth above. The method may further comprise after step (a) and before step (b) removing solid waste from said medium provided in step (a). The composition in the above specific embodiments may comprise between about 5% to about 10% RL.

In yet another embodiment, the method may further comprise after the sterilization step (b) and before the separation step (c) aging said sterilized medium of step (a). In yet another embodiment, after step (a) and before said medium is aged in (1), solid waste may be removed from medium provided.

In yet another embodiment, the method comprises two aging steps and may comprise the following steps:

(a) providing an aqueous medium (e.g., fermentation medium) comprising at least one rhamnolipid;

(b) aging said aqueous medium (e.g., fermentation medium) provided;

(c) non-filtration based sterilization of said medium provided in (b);

(d) aging said sterilized medium of (c) and (e) separating a RL containing liquid phase from waste in said aged and sterilized medium in (d) to obtain said composition.

In yet even another embodiment, a composition comprising rhamnolipids may be a clarified broth which comprises at least about 5%, 6%, 7%, 8% 9%, or 10% rhamnolipids by weight. In a particular embodiment, the method for obtaining the composition comprising RLs, particularly a clarified broth may, comprise before step (b) aging said medium provided in step (a) then subsequently (b) sterilizing said aged medium via chemical treatment, in particular, peroxide treatment (e.g., hydrogen peroxide, and organic peroxides such as benzoyl peroxide and peroxyacetic acid and inorganic peroxides such as lithium peroxide, sodium peroxide, barium peroxide), and/or ultraviolet light radiation treatment; (c) separating a RL containing phase from the solid waste in said sterilized medium and optionally further comprising (c)(1) additionally sterilizing said RL containing phase and (c)(2) separating a RL containing phase from solid waste in said sterilized RL containing phase to obtain said clarified broth. In a particular embodiment, said sterilization step in step (b) is via chemical treatment and/or ultraviolet radiation treatment and the sterilization step in step (c)(2) is via heat.

Also provided is a composition obtainable after sterilizing said aged medium. Further provided are sterilized compositions obtainable using steps (b) and/or (c)(1) set forth above.

The methods set forth above may further comprise a decolorization and/or deodorization step. The decolorization and/or deodorization treatment may be performed before and/or after the sterilization step. Also provided is a composition comprising decolorized and/or deodorized medium obtainable using the methods set forth above.

In even yet another embodiment, after step (c), fluid or liquid may be removed from the separated RL containing phase to obtain a solid composition for example, by evaporation. In a particular embodiment, said composition is in for example, powder form or granular form.

In even yet another embodiment, said composition comprising rhamnolipids is a concentrated clarified broth comprising at least about 30%, at least about 35%, at least about 40%, at least about 45%, at least about 50% or at least about 60% rhamnolipids by weight. In yet a more particular embodiment, said concentrated clarified broth may comprise between about 30-60% RL, about 30-40% RL or about 50-60% RL by weight.

In a particular embodiment, said medium provided in step (a) in the method set forth above is sterilized in step (b) by treating said medium with acid and said acidic medium obtained comprises a solid, liquid and oily phase and at least the liquid phase is removed and before step (c), the solid and optionally oily phases are neutralized to obtain a solution and in step (c) insoluble waste material is removed from said solution to obtain said composition comprising said concentrated clarified broth set forth above. Thus a method for obtaining concentrated clarified broth may comprise:

(a) providing aqueous medium (e.g., fermentation medium) comprising rhamnolipids (RLs);

(b) sterilizing said fermentation or culture medium provided in (a) via acid treatment to obtain an acidified liquid, oily and solid phase;

(c) removing said liquid phase obtained in (b) and treating said solid and optionally oily phase with base to obtain a neutralized solution;

(d) removing insoluble material from said solution obtained in (c) to obtain a composition comprising concentrated clarified broth comprising one or more rhamnolipids.

In yet another embodiment, the method for obtaining a composition comprising concentrated clarified broth, may further comprise an additional sterilization step and optionally a further separation step to remove insoluble waste from said solution. Furthermore, said method may further comprise after sterilization, decolorizing and/or deodorizing said sterilized concentrated clarified broth. The method may also further comprise removing liquid or fluid from said solution by evaporation obtained in step (c) to obtain a solid composition. The medium may be treated with acid and then neutralized either before or after the additional sterilization step.

In the methods set forth above, said solid and oily phases may be neutralized separately to obtain separate solutions. Alternatively, said solid and oily phases are combined and said combined solid and oily phases are neutralized to obtain a neutralized solution. Furthermore, in yet another embodiment, only the solid phase is neutralized.

The methods set forth above may further comprise decolorizing and/or deodorizing said composition. Additionally, said composition may be dried.

In another embodiment, a method for obtaining a composition comprising rhamnolipids which is a concentrated clarified broth comprising at least about 30%, at least about 35%, at least about 40%, at least about 45%, at least about 50% or at least about 60% rhamnolipids by weight, may further comprise before and/or after said additional sterilization step aging said medium provided.

In particular, said method comprises:

(a) providing an aqueous (e.g., fermentation) medium comprising one or more rhamnolipids;

(b) optionally removing insoluble waste from said medium provided;

(c) sterilizing said medium provided;

(d) aging said sterilized medium of (c);

(e) removing waste from said aged and sterilized medium;

(f) treating medium obtained in (e) with acid, wherein said acidic medium obtained comprises a solid, liquid and oily phase and at least the liquid phase is removed and the solid and optionally oily phases are neutralized to obtain a neutralized solution;

(g) removing solid waste from said neutralized solution of (f) to obtain said composition comprising said concentrated clarified broth.

Also provided are compositions comprising the neutralized solution obtainable according to the methods set forth above. Further provided are decolorized and/or deodorized compositions comprising at least about 30% RLs using or obtainable from methods set forth above.

The compositions obtained may be used as a surfactant in hand soaps, body washes, facial cleansers, tooth paste, shampoos, conditioners, conditioning shampoos, cosmetics, dish soap, laundry detergents, laundry pretreatment sprays, hard surface cleaners, porous surface cleaners, floor cleaners, automobile cleaners, enhanced oil recovery, wound dressings, agricultural anti-bacterials, anti-corrosion treatments, bioremediation, anti-stick films, anti-biofouling applications, fire extinguishing media, anti-virals, anti-molds, and anti-zoosporics. In one embodiment, the compositions containing higher amounts of RL (>30% wt/vol) or more particularly about (>50% wt/vol) obtained using the methods set forth above can be used to make a rhamnolipid based product that can displace an anionic surfactant such as sodium lauryl sulfate (SLS) in personal care and household cleaner markets given that certain anionic surfactants are often sold at a concentration of about 30% for some application.

DEFINITIONS

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this disclosure are incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

It must be noted that as used herein and in the appended claims, the singular forms "a," "and" and "the" include plural references unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. Thus the terms "comprising", "including," containing", "having" etc. shall be read expansively or open-ended and without limitation. When used herein the term "comprising" can be substituted with the term "containing" or sometimes when used herein with the term "having".

As defined herein, a "rhamnolipid" refers to a glycolipid that has a lipid portion that includes one or more, typically linear, saturated or unsaturated β-hydroxy-carboxylic acid moieties and a saccharide portion of one or more units of rhamnose.

The saccharide portion and the lipid portion are linked via a β-glycosidic bond between the 1-OH group of a rhamnose moiety of the saccharide portion and the 3-OH group of a β-hydroxy-carboxylic acid of the lipid portion. Thus the carboxylic group of one carboxylic acid moiety defines the end of the rhamnolipid. Where more than one rhamnose-moiety is included in a rhamnolipid, each of the rhamnose moieties not linked to the lipid portion is linked to another rhamnose moiety via a 1,4β-glycosidic bond. In embodiments where two or more β-hydroxy-carboxylic acids are present in a rhamnolipid, the β-hydroxy-carboxylic acid moieties are selected independently from each other. β-hydroxy carboxylic acid moieties of a respective plurality of β-hydroxy carboxylic acid moieties may in some embodiments be identical. In some embodiments they are different from each other.

As defined herein, the term "an aqueous medium" is a composition which comprises at least about 5% by weight of rhamnolipids or salts of rhamnolipids in water. In a particular embodiment, it comprises the product of a fermentation that has the ability to produce one or more rhamnolipids from at least one carbon source under fermentation conditions known in the art.

The terms "fermentation broth" and "fermentation medium" are synonymous and may be used interchangeably.

DETAILED DESCRIPTION

Provided herein is an organic solvent free-method for obtaining a composition comprising one or more rhamnolipids. In a particular embodiment, the rhamnolipid may have the structure (I)

In this formula, $R^9$ is a hydrogen atom (H) or an aliphatic group that has a main chain of one to about 46, such as one to about 42, one to about 40, one to about 38, one to about 36, one to about 34, one to about 30, one to about 28, including e.g. 2, 3, 4, 5, 6, 7, 8, 9, 10, 11, 12, 13, 14, 15, 16, 17, 18, 19, 20, 21, 22, 23, 24, 25, 26, 27 or 28 carbon atoms and one to about three, including two, oxygen atoms. In some embodiments, the main chain of the respective aliphatic group carries a terminal carboxylic acid group and/or an internal ester group. As an illustrative example in this regard, $R^9$ may be of the formula —CH($R^5$)—CH$_2$—COOR$^6$. In these illustrative moieties, $R^5$ may be an aliphatic moiety with a main chain that has a length from 1 to about 19, such as from 1 to about 17, from 1 to about 15, from 1 to about 13, about 2 to about 13, about 3 to about 13 or about 4 to about 13, including e.g. 2, 3, 4, 5, 6, 7, 8, 9, 10, 11 or 12 carbon atoms. $R^4$ in formula (I) is a hydrogen atom (H), or a rhamnopyranosyl moiety. $R^6$ is a hydrogen atom.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. Herein, an unsaturated aliphatic group contains one or more double bonds (alkenyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to about 5, to about 10, to about 15 or to about 20 carbon atoms. Examples of alkenyl moieties are straight-chain or branched hydrocarbon moieties which contain one or more double bonds. Alkenyl moieties generally contain about two to about twenty carbon atoms and one or more, for instance two, double bonds, such as about two to about ten carbon atoms, and one double bond. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3-dimethylbutyl. Both the main chain as well as the branches may furthermore contain heteroatoms as for instance N, O, S, Se or Si or a carbon atom may be replaced by one of these heteroatoms. An aliphatic moiety may be substituted or unsubstituted with one or more functional groups. Substituents may be any functional group, as for example, but not limited to, amino, amido, carbonyl, carboxyl, hydroxyl, nitro, thio and sulfonyl.

In a more particular embodiment, the rhamnolipid(s) or rhamnolipid salts in said structure has the structure (II):

wherein x is 1 or 2, y is 4, 6 or 8 and M is H, or a metal, such as alkali metals Li, Na, or K, alkali earth metals Mg or Ca, or transition metals Mn, Fe, Cu, or Zn. In the cases of the alkali earth and transition metals, multiple rhamnolipid salt moieties may associate with each metal. In a specific embodiment, the composition comprises a mixture of mono (where x=1) and di (where x=2) rhamnolipids where y and z are 6 and M is H or Na. The mono-rhamnolipid may be referred to as Rha-C10-C10, with a formula of $C_{26}H_{48}O_9$. The IUPAC Name is 3-[3-[(2R,3R,4R,5R,6S)-3,4,5-trihydroxy-6-methyloxan-2-yl]oxydecanoyloxy]decanoic acid. The di-rhamnolipid may be referred to as RhaRha-C10-C10, with a formula of $C_{32}H_{58}O_{13}$. The IUPAC name is 3-[3-[4,5-dihydroxy-6-methyl-3-(3,4,5-trihydroxy-6-methyloxan-2-yl)oxyoxan-2-yl]oxydecanoyloxy]decanoic acid. In a more specific embodiment, mono-rhamnolipid may be present in the amount of about from 30% of total rhamnolipid to about 50% of total and di-rhamnolipid may be present in the amount of about from 50% of total rhamnolipid to about 70% di-rhamnolipid. The composition in another embodiment comprises mono and di-rhamnolipids wherein the ratio of mono-rhamnolipids:di-rhamnolipids is from about 35:65 to about 55:45

In a most specific embodiment, the composition comprises the compounds set forth in Table 1.

TABLE 1

| Fatty acid chains | Mono- (x = 1) | Di- (x = 2) | y and z |
|---|---|---|---|
| C10-C10 | 28-40% | 42-60% | 6 |
| Other | 0-12% | 0-18% | y and/or z = 4 or 8 (and if 8, there may be a point of unsaturation |

As set forth above, the method comprises: (a) providing an aqueous medium comprising at least one rhamnolipid (RL); (b) non-mechanical sterilization of said medium provided in (a) and (c) separating a RL containing phase in the sterilized medium of (b) from waste to obtain said composition. Furthermore, in specific embodiments, aging, acidification, neutralization, drying, decolorization and/or deodorization steps may also be used.

Source of Medium

The aqueous medium provided comprising one or more rhamnolipids may be obtainable from a fermentation broth derived from and in particular, may be a result of a recombinant host cell producing rhamnolipids using methods known in the art or from a rhamnolipid producing microorganism. A recombinant host cell producing rhamnolipids may be a host cell, such as a bacterial cell that expresses a RhlA gene or ortholog thereof and/or a RhlB gene or ortholog thereof, and/or a RhlC gene or ortholog thereof, and/or RhlR gene or ortholog thereof, and/or RhlI gene or ortholog thereof, and/or RhlG gene or ortholog thereof and others.

The term "rhamnolipid-producing microorganism" as used herein, refers to any microorganism, such as bacteria, which has the capacity to synthesize/produce rhamnolipids under suitable conditions which includes but is not limited to bacterium of the phyla Actinobacteria, Fimicutes and Proteobacteria. In a particular embodiment, the rhamnolipid-producing microorganism is a bacterium of the Gammaproteobacteria class. In a further embodiment, the rhamnolipid-producing microorganism is a bacterium of the Pseudomonadales order. In yet another further embodiment, the rhamnolipid producing microorganism is a bacterium of the Pseudomonadacae family. In a further embodiment, the rhamnolipid-producing microorganism is a bacterium of the *Pseudomonas* genus, such as *P. alcaligenes*, *P. aeruginosa*, *P. chlororaphis*, *P. clemancea*, *P. collierea*, *P. fluorescens*, *P. luteola*, *P. putida*, *P. stutzeri* and *P. teessidea*. In a further embodiment, the rhamnolipid-producing microorganism is *P. aeruginosa*.

The host cell is cultured under conditions that allow RL production. A variety of carbon sources may be used such as a monosaccharide, e.g. glucose, a disaccharide, e.g. sucrose, an alcohol, e.g. glycerol, an alkane, e.g., n-hexadecane, a fatty acid such as caprylic acid (also termed octanoate), vegetable oils (fresh or waste; e.g., soybean oil) or mixtures thereof, organic acids (e.g. lactic acid, acetic acid, citric acid, propionic acid), alcohols (e.g. ethanol, glycerin), and mixtures of these; nitrogen sources such as ammonium sulfate, ammonium phosphate, urea, yeast extract, meat extract, peptone, and corn steep liquor; and other nutritional sources such as mineral salts and vitamins. The bacterial host cell will typically be exposed to a fermentation process. The bacterial host cell may for instance be in the logarithmic growth phase or in the stationary phase.

Sterilization

The aqueous (e.g., fermentation) medium provided is sterilized. In particular, the medium in the methods set forth above may be sterilized by non filtration methods using methods known in the art. These methods may be either heat based, chemical based or ultraviolet light radiation based. In a particular embodiment, the heat based treatment may be via moist heat sterilization, particularly autoclaving.

Alternatively, the fermentation medium may be treated chemically. In one particular embodiment, the chemical treatment may be via acidification, removal of solid waste and neutralization using procedures set forth below.

In another particular embodiment, the aqueous (e.g. fermentation) medium may be treated with peroxides such as hydrogen peroxide, lithium peroxide, sodium peroxide, barium peroxide, peroxyacetic acid, benzoyl peroxide, in particular, hydrogen peroxide using methods known in the art and set forth below.

In yet another embodiment, the aqueous medium may be irradiated with, for example, ultraviolet light irradiation.

In one embodiment, the aqueous medium (e.g., fermentation medium or broth) may be sterilized by one of the above procedures. In another embodiment, the fermentation media may be sterilized by more than one of the procedures set forth above and these sterilizations could be in any order.

Separation/Removal of Waste Products (Solid/Liquid (S/L) Separation)

Waste from the compositions and/or medium obtained using the medium set forth herein may be removed or separated from the composition using separation procedures known in the art. These procedures include but are not limited to, settling batch or continuous centrifugation or ultracentrifugation, which may be followed by decantation or filtration using procedures known in the art. The waste can be either a solid phase or a liquid phase, depending on where in the process the separation occurs.

Aging

The culture or fermentation medium may be aged by incubating for at least about 1 day and between about 24-72 hrs. at between about 0-30 C. This aging step may occur before and/or after one or more of the sterilization steps set forth above.

Acidification/Neutralization

Aqueous (e.g. Fermentation) medium may be concentrated or sterilized by treating with acid, removing liquid waste and then neutralizing the remaining solid and optionally oily phase or layer. In a particular embodiment, the aqueous medium may be treated with acid so the culture medium is adjusted to a pH of between about 1.5 to 2.5, preferentially, about 2.05 to about 2.15. The acid can be an organic acid such as acetic acid, or a mineral acid. In a preferred embodiment, the acid is a mineral acid, e.g. HCl, $H_2SO_4$, $HNO_3$, or $H_3ClO_4$. As a result, a liquid, oily and solid phase is generated. The liquid phase is removed using procedures known in the art and in a specific embodiment using methods set forth above (e.g., filtration, or centrifugation or settling combined with decanting).

The solid and optionally the oily phase are neutralized to a pH greater than about 5.5, preferably between about 6.5-7.5, more preferably between about 6.9-7.1. In a specific embodiment, the solid and optionally oily phase is treated with a solid, dry mineral base (e.g., NaOH, KOH, LiOH, $NaHCO_3$). In the event that both the solid and oily phases are neutralized, these phases may be combined and neutralized or alternatively neutralized separately. After neutralization, solid waste is removed by methods set forth above, including but not limited to filtration, settling or centrifugation and decantation. The neutralized material may also be subjected to a further sterilization step, as set forth above.

Decolorization/Deodorization

The aqueous medium (e.g., fermentation medium or broth) may be decolorized and/or deodorized using procedures know in the art. In a particular embodiment, chemical and/or ultraviolet or visible radiation treatment is used.

In a specific embodiment, said decolorization and/or deodorization step may be accomplished via peroxide treatment using either hydrogen peroxide or organic (e.g., benzoyl peroxide or peroxyacetic acid) or inorganic peroxide (e.g., lithium peroxide, sodium peroxide, barium peroxide). In a particular embodiment, the aqueous medium (e.g., fermentation medium or broth) may be treated with peroxide, particularly, hydrogen peroxide, at a concentration of about 1-5% v/v for about 48-120 hours and more particularly between about 3-4% v/v for about 72-96 hours.

Alternatively, the aqueous medium may be decolorized and/or deodorized via ultraviolet or visible radiation from 350-550 nm, preferentially 400-450 nm. The dose of radiation needs to be at least about 100 J/g of rhamnolipids, preferentially at least about 1 kJ/g, more preferentially at least about 10 kJ/g.

This aqueous medium may be decolorized and/or deodorized before and/or after sterilization and before or after the acidification and neutralization process described above.

Liquid Removal

In another embodiment, the liquid may be removed after removal of solid waste using methods known in the art, with the proviso that it does not follow decolorization and/or deodorization by peroxide treatment. These include but are not limited to heat, evaporation, freeze drying (lyophilization), drum drying.

DESCRIPTION OF SPECIFIC EMBODIMENTS

Figure 1:
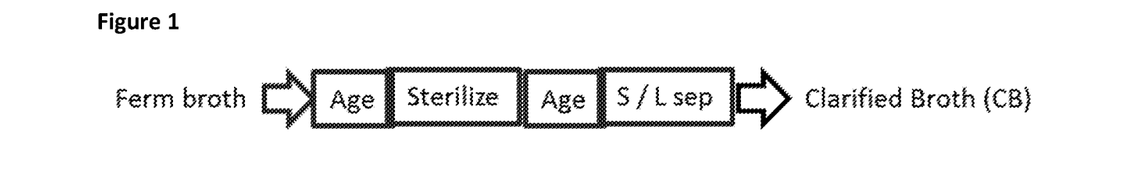
FIG. 1 schematically shows an organic solvent free method for obtaining rhamnolipid rich clarified broth (CB).

Example 1: A Process to Recover a Rhamnolipid (RL) Rich Solution (Clarified Broth) from Fermentation Broth without the Use of Organic Solvent Provided herein is a process to recover rhamnolipids from fermentation broth in a dilute solution containing at least 50 g/L of a mixture of di- and mono-rhamnolipids without the use of organic solvents. The general scheme that is used is depicted in FIG. 1.

The process utilizes aging at room temperature, followed by autoclaving, and standard solid/liquid separation techniques to separate clarified rhamnolipid rich solution contained at least 50 g/L from bacterial cell matter. In particular, the rhamnolipid containing broth is generated from the fermentation by *Pseudomonas aeruginosa* at pH 6.2-6.5 at 37 C for 48-72 hours with soybean oil as the feedstock. The final pH of fermentation broth prior to aging is in the range of 6.4-6.5. After aging for ~48 hours at room temperature, the fermentation broth is sterilized by steam heating or autoclaving. After solid/liquid separation, the rhamnolipid solution is clear and ready to be used. The dark brown color of the rhamnolipid solution can be reduced with the addition of hydrogen peroxide at 2-3% v/v over 72-96 hrs. at room temperature. Other peroxides can also be used in this step, including organic (e.g., benzoyl peroxide or peroxyacetic acid) or inorganic peroxide (e.g., lithium peroxide, sodium peroxide, barium peroxide). Rhamnolipid rich solution (>5% active) is obtained.

The clarified rhamnolipid rich solution, if not treated with peroxide, can also be lyophilized to produce a lightly colored powder. A rhamnolipid rich powder (>75% active) is obtained.

Figure 2:
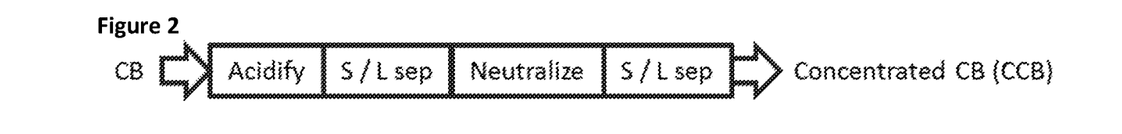
FIG. 2 schematically shows were the CB is concentrated by acid/base treatment to obtain concentrated clarified broth (CCB).

Example 2: Isolation of an Aqueous Solution of Rhamnolipids by Precipitation from Clarified Fermentation Broth and Redissolution in Base and the Composition that Results from the Process The current process starts with the clarified broth obtained in Example 1 and is depicted schematically in FIG. 2. As described in Example 1, clarified broth is made by allowing fermentation broth that ends at a pH of 6.0 to 6.5 to age under ambient conditions for about 2 days. The biomass settles to the bottom of the vessel used for this aging process and the clear supernatant, after removal, is clarified broth. The next step in the process is to add acid, such as concentrated sulfuric acid, until the pH is about 2.1. The rhamnolipids precipitate out of solution and form a solid phase and an oily liquid phase at the bottom of the vessel used for this step. The separation of the solid and oily liquid phases can be sped up by centrifugation. The solid and oily liquid phases are separated from the aqueous top phase or layer, which can be discarded or recycled. The combined solid and oily liquid rhamnolipid containing phases are then treated with a solid base, such as sodium hydroxide, until the pH reaches about 7.0. This produces a viscous solution of rhamnolipids in water with a concentration of about 25 to 30%. The final step is to centrifuge the 25-30% rhamnolipid solution and decant the liquid final product away from the pellet formed from any remaining solids. This liquid can be lyophilized (freeze dried) to produce a dry solid product.

Figure 3:
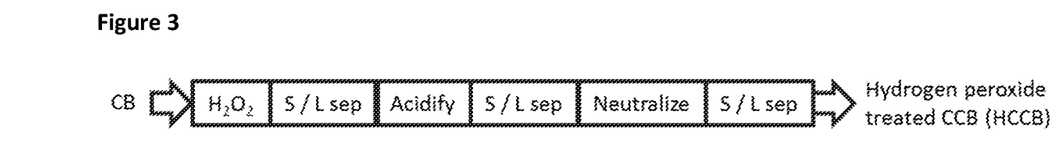
FIG. 3 schematically shows obtaining CCB from hydrogen peroxide treated CB.
Figure 4:
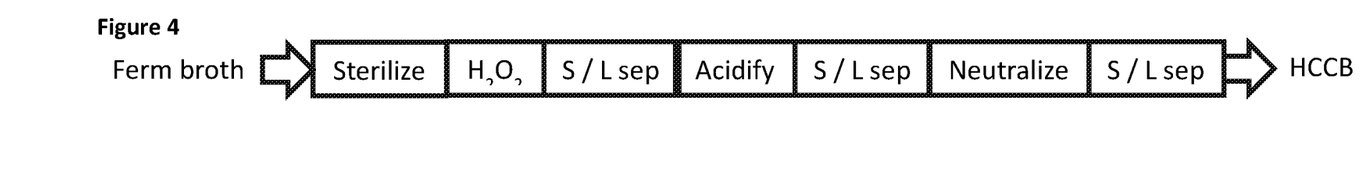
FIG. 4 schematically shows obtaining CCB from hydrogen peroxide treated sterilized fermentation medium.

Example 3: Non-Organic Solvent Concentrated Process to Produce 35-40% Rhamnolipid Solution Using a pH Shift Provided is a process for the production of 30-40% rhamnolipid solution using a pH shift starting with "reduced color and odor clarified broth" as described in Example 1 or "reduced color and odor sterilized fermentation broth" and are schematically depicted in FIGS. 3 and 4.

The "reduced color and odor clarified broth" and "reduced color and odor sterilized fermentation broth" can be obtained by adding 3-5% v/v hydrogen peroxide to clarified broth or sterilized fermentation broth respectively. After 72-96 hours at room temperature, the color of the clarified rhamnolipid rich solution is slightly yellow with no loss in rhamnolipids and odor is reduced. After that, the reduced color and odor clarified broth is filtered at 1 micron by cross flow filtration or solids are removed by centrifugation followed by decanting. The concentrated acid such as sulfuric acid is added into the filtrate (permeate) or supernatant until the pH is about 2.1. The mixture is then allowed to separate into a rhamnolipid rich layer made up of a solid phase and an oily liquid phase at the bottom of the container. The combined solid and oily liquid rhamnolipid containing phases are then separated from the aqueous top layer and treated with a solid base, such as sodium hydroxide, until the pH reaches about 7.0. This produces a viscous solution of rhamnolipids in water.

The final step is to centrifuge the resulting rhamnolipid solution and remove the liquid final product from the pellet formed from any remaining solids. The final liquid product is 30-40% rhamnolipids Example 4: Process for Isolating Rhamnolipids from Fermentation Broth with Sterilization at End of the Process and Materials Produced During the Process The process, schematically depicted in FIG. 5, begins by doing a solid/liquid separation process such as centrifugation or filtration of fermentation broth that still contains a living organism that produces rhamnolipids. The clarified liquid product is then acidified to pH 2.1 using concentrated sulfuric acid, or another concentrated, strong mineral acid. After settling or centrifugation, the water layer is decanted away from the denser product, which is an oily layer and a solid layer. This oily and/or solid layer is neutralized to pH 7 with a solid base such as sodium hydroxide, resulting in a solution. A final solid/liquid separation step is done to remove any remaining undissolved impurities. The liquid is then sterilized by, for example, autoclaving.

Example 5: Non-Organic Solvent Concentrated Process to Produce 50-60% Rhamnolipid Solution Using a pH Shift Provided is a modification of the process disclosed in Example 3, "Non-organic solvent concentrated process to produce 30-40% rhamnolipid solution using a pH shift" to produce 50-60% rhamnolipid solution.

A preparation of clarified broth and the acid precipitation of the clarified broth with concentrated sulfuric acid (95-98 wt %) to pH 2.1 remain the same as disclosed in Example 3. After adding 95-98 wt % sulfuric acid to the clarified broth until the pH is at 2.1, the mixture is then allowed to separate into a rhamnolipid rich layer made up of a solid phase and an oily liquid phase at the bottom of the container. However, to obtain 50-60% rhamnolipid solution, the oily material and the solid, are separated using, for example centrifugation. After centrifugation, the solid is obtained at the bottom and the oily material is at the middle while the aqueous top layer is at the top of the vessel. The solids are then separated from oily liquid rhamnolipid containing phases and are treated with a solid base, such as sodium hydroxide until the pH reaches about 7.0 at which the product liquefies.

The final step is to centrifuge the resulting rhamnolipid solution and remove the liquid final product from the pellet formed from any remaining solids. The final liquid product is 50-60% rhamnolipids and is part of the invention. This liquid may be lyophilized (freeze dried) to produce a dry solid product, which is also part of the invention.

Example 6: Process for Isolating Rhamnolipid from Fermentation Broth Before Sterilization to Obtain High Rhamnolipid Concentration without Solvent Extraction This process is a modification of the process described in Example 5: "Non-organic solvent concentrated process to produce 50-60% rhamnolipid solution using a pH shift" to produce 50-60% rhamnolipid solution but at a higher yield since it includes the oily layer obtained after acid precipitation and thus, increasing the recovery of rhamnolipids.

Figures 5, 6:
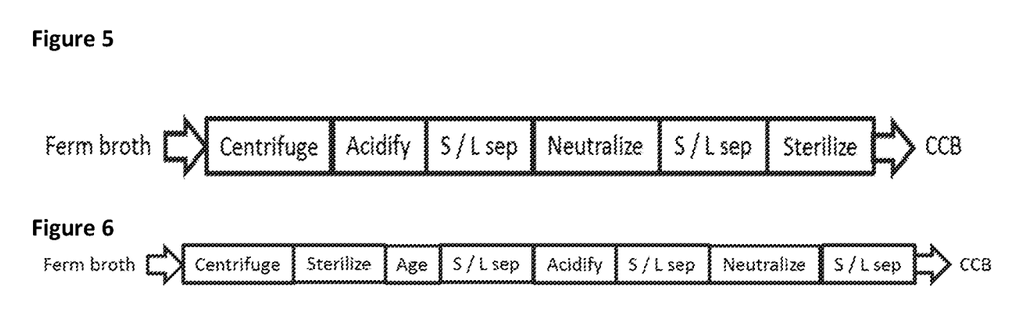
FIG. 5 schematically shows obtaining CCB by first performing a separation step on the fermentation broth and performing the sterilization step later in the process.
FIG. 6 schematically shows a method for obtaining CCB by performing separation, sterilization, aging and acidification steps.

The process is depicted in FIG. 6. It begins with fermentation broth that contains rhamnolipids and biomass from cells that produced the rhamnolipids, preferentially *Pseudomonas aeruginosa*. First, centrifugation is performed at at least 7500 g for at least 5 min. A clarified broth (CB) is then separated from microbial cells (solid) and is sterilized via steam autoclave. The CB is then allowed to settle, preferably overnight, prior to being centrifuged or filtered to remove any additional solids that precipitated out during settling.

This further clarified CB is then acidified to pH 2.1 using concentrated sulfuric acid, or another concentrated, strong mineral acid. The acidified clarified broth is part of the invention. After settling or centrifugation, the water layer is decanted away from a solid layer. The solid is then treated with a solid base, such as sodium hydroxide, until the pH reaches about 7.0. The result is a liquid with 50-60% rhamnolipids. This liquid can be lyophilized (freeze dried) to produce a dry solid product.

By centrifuging immediately after fermentation is stopped and then ageing the product as described in Example 1, a Clarified Broth (CB) is produced that can be further processed. This solves the problem that solid/liquid separation of fermentation broth can be difficult.

The overall process produces a product that is a high concentration of rhamnolipid biosurfactant cost effectively with a recovery rate of the rhamnolipids in the original fermentation broth of about >80%. This solves the problem that it is perceived that isolating products from rhamnolipid fermentations is too expensive to be commercially viable.

What is claimed is:

1. An organic solvent-free process for obtaining a composition comprising one or more rhamnolipids (RLs), wherein said composition comprising rhamnolipids is a concentrated clarified broth comprising at least about 30% rhamnolipids by weight comprising:
    (a) providing an aqueous medium comprising at least one rhamnolipid;
    (b) removing solid waste from said medium provided in step (a);
    (c) treating said medium obtained in step (b) with acid to obtain an acidic medium, wherein said acidic medium obtained comprises a solid, aqueous liquid and oily phase;
    (d) removing at least the aqueous liquid phase obtained in step (c);
    (e) neutralizing the solid and optionally oily phases obtained in step (c) to produce a neutralized solution;
    (f) removing insoluble waste material from said neutralized solution of step (e) to obtain said composition.

2. The process according to claim 1, wherein said method further comprises a sterilization step before and/or after said medium is treated with acid in step (c) and optionally an additional separation step to remove insoluble waste from said solution before and/or after said sterilization step.

3. The process according to claim 1, which further comprises after sterilization, decolorizing and/or deodorized said sterilized concentrated clarified broth.

4. The process according to claim 1, which further comprises removing water from said solution obtained in step (f).

5. The process according to claim 1, wherein said solid and oily phases are neutralized separately to obtain separate solutions.

6. The process according to claim 1, wherein said solid and oily phases are combined and said combined solid and oily phases are neutralized to obtain a neutralized solution.

7. The process according to claim 1, wherein said method further comprises before and/or after said sterilization step aging said medium provided.

8. A composition comprising a neutralized solution obtainable according to the method of claim 1.

9. A composition comprising a decolorized and/or deodorized concentrated clarified broth obtainable according to the method of claim 3.

10. A composition comprising the aged medium obtainable according to the method of claim 7.

* * * * *